United States Patent [19]

Samson et al.

[11] Patent Number: 5,090,959
[45] Date of Patent: Feb. 25, 1992

[54] IMAGING BALLOON DILATATION CATHETER

[75] Inventors: Gene L. Samson, Fremont; Michael Aita, Mountain View, both of Calif.

[73] Assignee: Advanced Cardiovascular Systems, Inc., Santa Clara, Calif.

[21] Appl. No.: 584,423

[22] Filed: Sep. 13, 1990

Related U.S. Application Data

[63] Continuation of Ser. No. 222,316, Jul. 19, 1988, abandoned, which is a continuation of Ser. No. 45,076, Apr. 30, 1987, abandoned.

[51] Int. Cl.⁵ .................................. A61M 25/10
[52] U.S. Cl. .............................. 604/96; 606/194; 128/6
[58] Field of Search ........................ 128/4–6, 128/398; 606/191, 194, 7; 604/96–104

[56] References Cited

U.S. PATENT DOCUMENTS

| | | | |
|---|---|---|---|
| 3,866,599 | 2/1975 | Johnson | 604/21 |
| 4,040,413 | 8/1977 | Ohshiro | 604/21 |
| 4,445,892 | 5/1984 | Hussein et al. | 128/344 |
| 4,448,188 | 5/1984 | Loeb | 604/96 |
| 4,470,407 | 9/1984 | Hussein | 128/6 |
| 4,638,805 | 1/1987 | Powell | 128/344 |
| 4,684,363 | 8/1987 | Ari et al. | 128/344 |
| 4,737,142 | 4/1988 | Heckele | 128/6 |
| 4,756,303 | 7/1988 | Kawashima et al. | 128/6 |
| 4,770,653 | 9/1988 | Shturman | 604/21 |
| 4,773,396 | 9/1988 | Okazaki | 128/6 |
| 4,773,899 | 9/1988 | Spears | 128/344 |
| 4,781,681 | 11/1988 | Sharrow et al. | 604/96 |
| 4,892,099 | 1/1990 | Ohkawa et al. | 606/194 |

FOREIGN PATENT DOCUMENTS

| | | |
|---|---|---|
| 0112148 | 6/1984 | European Pat. Off. |
| 0122089 | 10/1984 | European Pat. Off. |
| 0345051 | 12/1989 | European Pat. Off. |
| WO83/01893 | 6/1983 | PCT Int'l Appl. |
| 8502101 | 5/1985 | PCT Int'l Appl. |
| 0654214 | 2/1986 | Switzerland ................ 604/101 |

Primary Examiner—C. Fred Rosenbaum
Assistant Examiner—William H. Lewis
Attorney, Agent, or Firm—Fulwider Patton Lee & Utecht

[57] ABSTRACT

An imaging balloon dilatation catheter having an elongate flexible tubular member with proximal and distal extremities. An inflatable balloon is carried by the tubular member near the distal extremity thereof. The tubular member has a plurality of lumens formed therein, an illuminating set of optical fibers is disposed in one of the lumens and extends through the length of the tubular member. An imaging bundle of optical fibers extends through another one of the lumens of the tubular member. A lens is carried by the distal extremity of the tubular member and supplies an image to the bundle of imaging optical fibers. The flexible elongate member is provided with a flow passage in communication with the interior of the balloon for inflating and deflating the balloon.

37 Claims, 2 Drawing Sheets

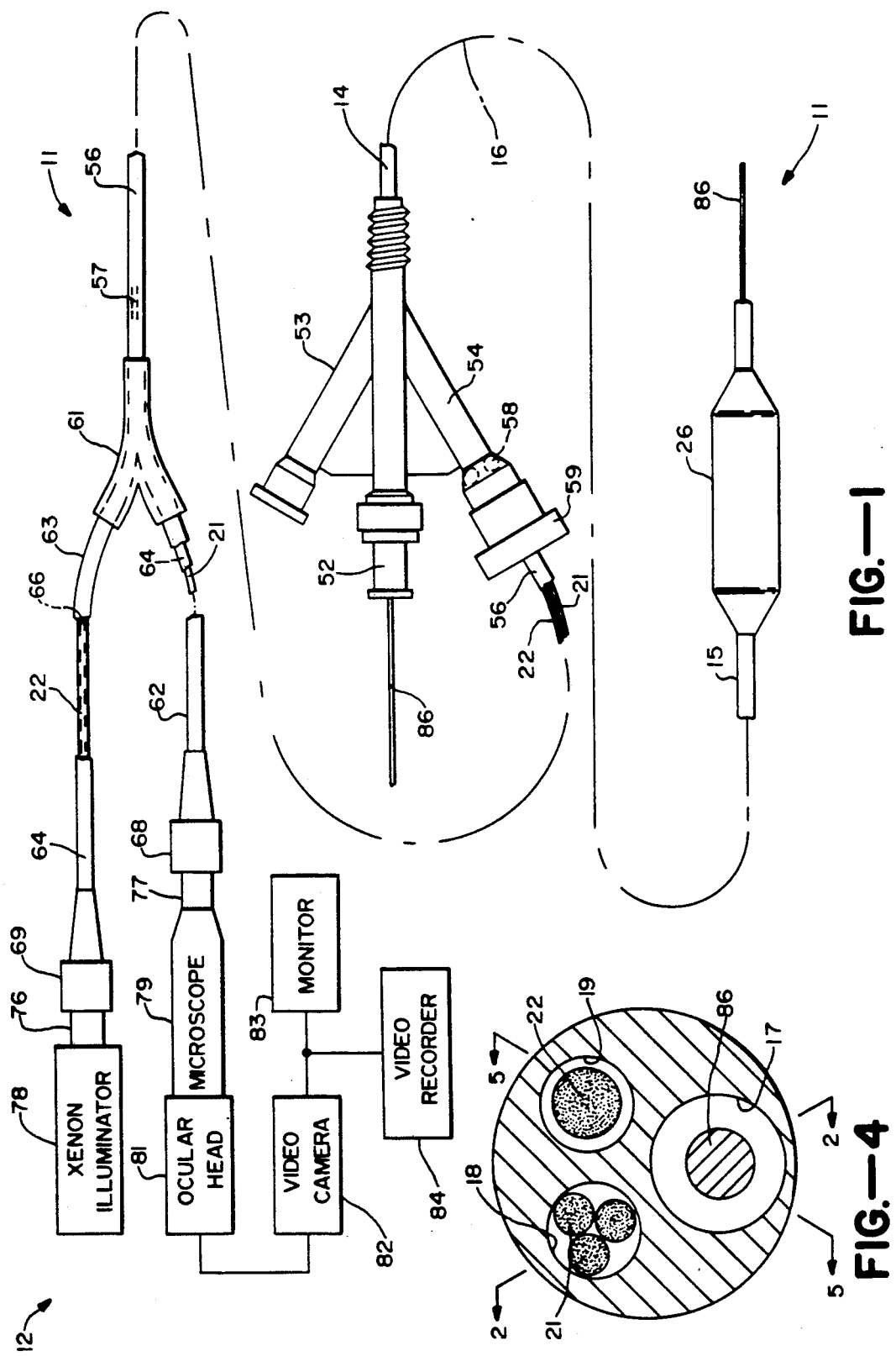

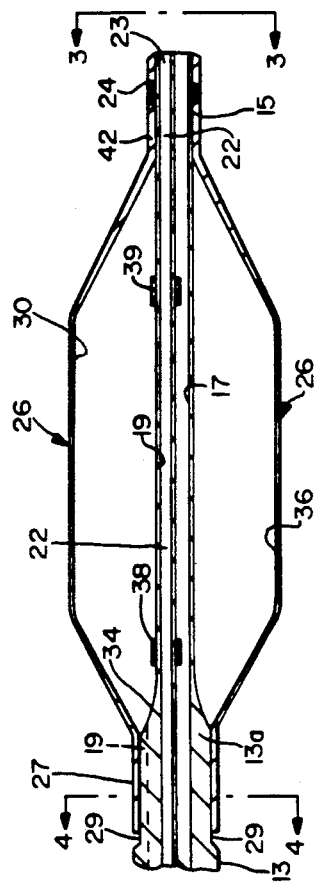
FIG.—2
FIG.—5
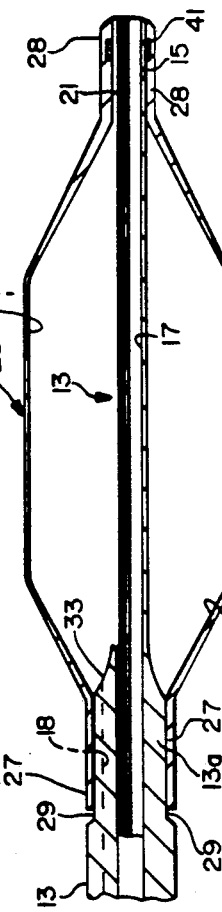
FIG.—6
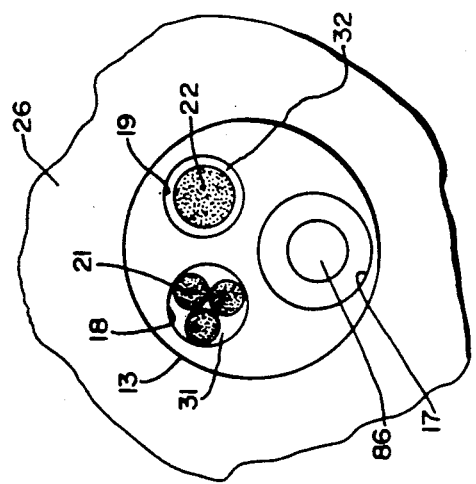
FIG.—3
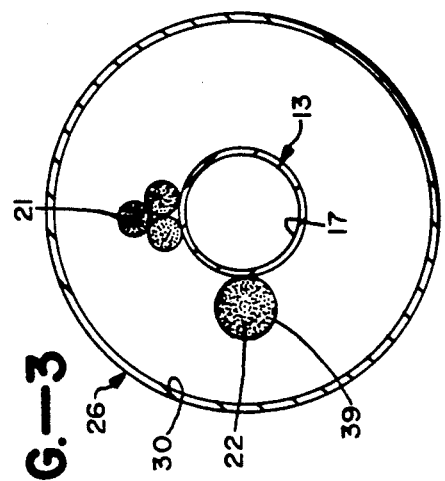
FIG.—7

IMAGING BALLOON DILATATION CATHETER

This application is a continuation of application Ser. No. 222,316, filed July 19, 1988, which is a continuation of U.S. Ser. No. 045,076 filed 4/30/87, both now abandoned.

This invention relates to imaging balloon dilatation catheters and more particularly to imaging balloon dilatation catheters for use in angioplasty.

Angioscopes have heretofore been provided by numerous manufacturers for many years. However, they have not been made small enough so that they can be used with dilatation catheters particularly those which travel over a guidewire. There is therefore a need for a balloon dilatation catheter which has imaging capabilities.

In general, it is an object of the present invention to provide an imaging balloon dilatation catheter which has imaging capabilities.

Another object of the invention is provide a catheter of the above character which can be utilized in very small vessels.

Another object of the invention is to provide a catheter of the above character which can be utilized in the cardiovascular system.

Another object of the invention is to provide a catheter of the above character in which a central lumen is provided for the angioscope.

Another object of the invention is to provide a catheter which is particularly useful in angioplasty.

Additional objects and features of the invention will appear from the following description in which the preferred embodiment is set forth in detail in conjunction with the accompanying drawings.

FIG. 1 is a schematic block diagram of an imaging balloon dilatation catheter incorporating the invention and the associated apparatus utilized therewith.

FIG. 2 is an enlarged side elevational view of the distal extremity of the imaging balloon dilatation catheter shown in FIG. 1 taken along the line 2—2 of FIG. 4 and showing the guide wire removed.

FIG. 3 is a cross sectional view taken along the line 3—3 of FIG. 2.

FIG. 4 is a cross sectional view taken along the line 4—4 of FIG. 2.

FIG. 5 is a cross sectional view taken along the line 5—5 of FIG. 4.

FIG. 6 is a cross sectional view similar to FIG. 5 showing an alternative embodiment of an imaging balloon catheter incorporating the present invention.

FIG. 7 is a cross sectional view taken along the line 7—7 of FIG. 6.

In general the imaging balloon dilatation catheter of the present invention is comprised of elongate flexible tubular member having proximal and distal extremities. An inflatable balloon is carried by the tubular member near the distal extremity thereof. The tubular member has a balloon inflation lumen extending therethrough from the proximal extremity to the balloon and opening into the interior of the balloon. The tubular member also has a guidewire lumen extending therethrough. An illuminating set of optical fibers extends through the tubular member from the proximal extremity to the distal extremity and an imaging set of optical fibers also extends through the tubular member from the proximal extremity to the distal extremity.

More in particular as shown in the drawings, the imaging balloon dilatation catheter and associated apparatus as shown in FIG. 1 is comprised of imaging balloon dilatation catheter 11 and associated apparatus 12. The imaging balloon dilatation catheter 11 consists of an elongate flexible tubular member 13 which is formed of a suitable material such as polyethylene. The elongate flexible tubular member 13 is provided with proximal and distal extremities 14 and 15 respectively and forms a shaft 16. At least three lumens 17, 18 and 19 are provided in the elongate flexible tubular member 13 with the lumen 17 being identified as a guidewire lumen, the lumen 18 being identified as the illumination optical fiber lumen and the lumen 19 being identified as the imaging optical fiber lumen. The lumens 18 and 19 for reasons hereinafter described can also be identified as inflation/deflation lumens. The guidewire lumen 17 extends throughout the length of the elongate flexible member from the proximal extremity 14 to the distal extremity 15. The lumens 17, 18 and 19 can have suitable diameters as for example the guidewire lumen can have a diameter of 0.021 inches and the lumens 18 and 19 a diameter of 0.015 inches and the elongate flexible tubular member 13 can have a suitable outside diameter as for example 0.056 inches, alternatively the lumens can all be of the same size. The elongate flexible tubular member 13 can have a suitable length as for example approximately 175 cm to provide the shaft 16 extending between the proximal and distal extremities 14 and 15.

A plurality of discrete illumination optical fibers 21 are provided in the lumen 18 as for example three of such fibers as shown. The illumination optical fibers can be of any suitable type and can be relatively inexpensive. It is only necessary that they have a good bending radius as for example be capable of withstanding bends as small as 1 cm in diameter. They also should have a large numerical aperture as, for example, 0.60.

A bundle 22 of imaging optical fibers is provided in the lumen 19. In order to achieve a suitable image, it is desirable that at least approximately 2,000 optical elements or optical fibers comprise the bundle. The bundle 22 also must have a good bending radius so that the catheter can be utilized for negotiating tortuous vessels in the human body. The type of fibers utilized in the imaging bundle 22 also can be a conventional type as for example of the type disclosed in U.S. Pat. No. 4,135,901.

A gradient index lens 23 is provided at the distal extremity 15 of the elongate flexible tubular member 13. The lens 23 serves to provide an image on its backside which is the same diameter as the bundle 22 which serves to place in that image the entire field of view which is viewed by the lens 23 at the distal extremity of the elongate flexible tubular member 13. The lens 23 is secured to the distal extremity of the bundle 22 by a suitable means such as an epoxy 24. The lens 23 can be recessed by a slight amount as for example 1 mm from the distal extremity of the flexible elongate tubular member 13 so as to protect the lens and also to prevent it from being broken off or scraped off during use of the catheter.

An inflatable balloon 26 is provided on the distal extremity 15 of the elongate flexible tubular member 13. The balloon 26 itself is provided with necked down proximal and distal extremities 27 and 28. The proximal extremity 27 is secured to a necked down portion 13a of the elongate flexible tubular member 13 by suitable means such as an adhesive 29. The necked down portion 13a can be necked down to a suitable diameter as for example 0.047 inches in outside diameter. The distal extremity 28 of the inflatable balloon 26 can be shrunk onto the distal extremity 15 of the tubular member 13 by application of heat to the same to provide a liquid-type seal. Self-venting means of the type described in U.S. Pat. No. 4,638,805 can be provided for venting the interior 30 of the balloon 26 to ambient. It should be appreciated that if desired instead of a separate balloon an integral balloon can be provided which is formed integral with the elongate flexible tubular member 13.

Means is provided for inflating and deflating the balloon 26 and consists of flow passages 31 and 32 which are provided in the lumens 18 and 19. The flow passages 31 and 32 are provided by the remaining space within the lumens 21 and 22 which are not occupied by the optical fibers 21 in the lumen 18 and the bundle 22 in the lumen 19. Cutouts 33 and 34 are provided in the elongate flexible tubular member 13 within the interior of the balloon 36 which are in communication with the flow passages 31 and 32 respectively. As hereinafter described, the flow passages 31 and 32 can be used for inflating and deflating the balloon 26. Because the cutouts 33 and 34 have been provided, the elongate tubular member 13 within the balloon 26 is of a reduced diameter as for example 0.043 inches.

A pair of balloon markers 38 and 39 are provided near the distal and proximal extremities of the balloon 26. These spaced apart balloon markers 38 and 39 can be formed of a suitable material such as platinum wire wrapped around the bundle 22 of imaging of optical fibers. An additional marker 41 has been provided for indicating the distal extremity of the catheter 11 and consists of a metallic band of a suitable radio opaque material such as gold. The marker 41 is provided over the distal extremity of the tubular member 13 and is encased within the distal extremity 28 of the balloon 26 and is positioned immediately to the rear of the lens 23.

The proximal extremity 14 of the tubular member 13 terminates in a three-arm adapter 51 which has a central arm 52 and side arms 53 and 54. The central arm 53 is in communication with the guidewire lumen 17. Thus the central arm 52 can be utilized for introducing the guidewire or it can be utilized for introducing radiographic contrast agents or flushing agents through the lumen 17. The side arm 53 serves as the balloon inflation/deflation port and is in communication with both of the lumens 18 and 19.

The other side arm 54 carries another elongate flexible tubular member 56 formed of a suitable material such as plastic which can have a suitable diameter as for example an outside diameter of 0.070 inches and inside diameter of 0.040 inches. The tubular member 56 extends into the side arm 54 and terminates therein and has the illumination optical fibers 21 and the bundle 22 of imaging fibers extending through the lumen 57 provided therein. An O-ring 58 is provided within the side arm 54 and surrounds the elongate tubular member 56. A knob 59 is mounted on the side arm 54 and is adapted to engage the O-ring 58 to form a liquid tight seal with respect to the elongate tubular member 56 to prevent the escape of blood through the side arm 54. The elongate tubular member 56 has a suitable length as for example 35 cm. At a junction defined by a Y-shaped reinforcing member 61, the illumination optical fibers 21 and the bundle of imaging fibers 22 are separated and placed in two additional elongate tubular members 62 and 63 having a suitable outside diameter such as 0.040 inches and an inside diameter of 0.030 inches to provide lumens 64 and 66 extending through the members 62 and 63. The illumination optical fibers 21 extend through the lumen 64 in the elongate member 62 and the bundle 22 of imaging optical fibers extends through the lumen 66 of the elongate member 63. The elongate tubular members 62 and 63 have a suitable length as for example 25 cm. The proximal extremities of the flexible elongate members 62 and 63 and the optical fibers 21 and 22 carried therein are connected to conventional type connectors utilized in fiberoptics as for example male-type connectors 68 and 69 identified as SMA. The connectors 68 and 69 are adapted to be mated with female SMA connectors 76 and 77 respectively. The connector 76 is mounted on Xenon illuminator 78 of a conventional type which supplies light to the illumination optical fibers 21. The connector 77 is adapted to be mounted on XYZ stage (not shown) of a microscope 79 which is provided with an ocular head 81 which can be used for viewing by the human eye and also for coupling into a video camera 82. The video camera 82 produces a signal which is supplied to a video monitor 83 and a video recorder 84.

Operation and use of the catheter 11 and the associated apparatus 12 may now be briefly described as follows. The balloon 26 is inflated outside the patient's body by introducing a balloon inflation medium through the balloon inflation port 53. Any air in the balloon is vented through the self-vent holes (not shown). The vent holes are of a size that will permit the escape of air but will prevent the escape of liquid therethrough. As soon as the air has been removed from the balloon 26 the balloon 26 can be deflated. Let it be assumed that it is desired to perform an angioplasty with the catheter 11. The catheter 11 can be introduced in the conventional manner over a guidewire 86 which is introduced through the central arm 52 and through the guidewire lumen 17 until it extends beyond the distal extremity of the same. The tip of the guidewire 86 is advanced into the stenosis to be treated and thereafter, the balloon 26 is advanced over the guidewire and is properly positioned within the stenosis. The positioning of the guidewire 86 and the catheter 11 can be observed on a fluoroscope. The balloon 26 is then inflated by introducing a suitable balloon inflation medium through the side arm 53 so that it can pass through the flow passages 31 and 32 provided in the lumens 18 and 19. After the balloon 26 has been inflated to the desired pressure for a suitable period of time, it is again deflated and the balloon 26 is withdrawn from the stenosis with the guidewire still in place. The balloon 26 is then reinflated proximal of the stenosis to block the flow of blood through the stenosis. A suitable flushing medium such as a saline solution is introduced through the guidewire and flushing lumen 17 so that a clear area is produced in front of the lens 23.

Assuming that the apparatus which is shown in FIG. 1 is connected to the catheter 11, suitable illumination is provided in the area of the stenosis through the illumination optical fibers 21. The image which is seen by the lens 23 to be viewed through the fiberoptic bundle 22 can be viewed through the monitor 83 or directly through viewing the ocular head 81 by the human eye. At the same time, a video recording can be made on the video recorder 84 of what is being seen. If the opening which has been formed in the stenosis and being imaged and viewed is satisfactory, the balloon 26 can be deflated and the catheter 11 removed from the vessel of the patient. However if it is found that the opening of the stenosis is not satisfactory, the guidewire 86 can then again be reinserted into the central arm 52 through the guidewire lumen 17 and through the stenosis. The balloon 26 of the catheter 11 can then be readvanced and the balloon can be reinflated to a suitable pressure for a suitable period of time to see if it is possible to further enlarge the opening in the stenosis. Thereafter, the balloon can be deflated and removed to a region just proximal of the stenosis and reinflated to stop the flow of blood. The guidewire 86 again can be removed and a flushing solution introduced through the lumen 17 to provide a clear field of view for the lens 23. The size of the opening through the stenosis can again be observed to see whether or not the size of the opening has been increased to provide a more satisfactory flow through the stenosis. If necessary, the procedure hereinbefore described can be repeated to ensure that a sufficient enlargement has been obtained.

If desired, a pressure measurement can be made by measuring the pressure at the distal extremity of the catheter 11 by use of the lumen 17. In addition it should be appreciated that the video signal which is supplied from the video camera 82 can be supplied to a computer so that it can be computer enhanced if that is desirable.

After the desired procedures have been completed the catheter 11 can be removed from the patient to complete the procedure.

An alternative embodiment of the imaging balloon dilatation catheter incorporating the present invention is shown in FIGS. 6 and 7. As shown therein, this catheter is very similar to that shown in FIGS. 2, 3, 4 and 5, with the exception that the plastic which forms the lumens 18 and 19 is removed from the interior of the balloon at the distal extremity 28. This makes it possible to reduce the outside diameter of the distal extremity from 0.060 to 0.062 for the embodiments shown in FIGS. 2-5 to 0.052 to 0.054 inches for the embodiment which is shown in FIGS. 6 and 7. In addition, the elimination of this plastic within the balloon decreases the stiffness of the distal extremity of the catheter facilitating negotiation of tortuosities in the vessel in which the catheter is introduced.

In fabricating the construction shown in FIGS. 6 and 7, rather than removing the plastic which forms the lumens 18 and 19 within the balloon 26, before mounting the balloon on the elongate flexible tubular member 13, the elongate flexible tubular member 13 can be terminated by cutting off the same at a point distal to the interior of the balloon 26. A separate tubular member (not shown) which can serve as a guide wire lumen 17 is provided and can be bonded to the tubular member 13 by suitable means such as an adhesive or by heat staking. Thereafter, the illuminating optical fibers 21 can be introduced through the lumen 18 until they extend beyond the point where the lumen terminates and to the distal extremity of the additional tubular member (not shown) which has been secured to the tubular member 13. Similarly, the bundle 22 of imaging optical fibers 22 can be inserted through the imaging optical fiber lumen 19 in a similar manner so that it extends beyond the lumen 19 to the distal extremity of the additional tubular member. Thereafter, the balloon 26 can have its proximal extremities secured to the flexible elongate tubular member 13. The distal extremity 28 of the balloon 26 can then be bonded to the distal extremity of the additional tubular member by suitable means such as an adhesive. As can be seen, this construction will also provide a reduced cross-sectional area at the distal extremity of the catheter as, for example, by reducing the diameter by the same amounts as specified for the embodiments shown in FIGS. 6 and 7. Such an embodiment will also have reduced stiffness and increased flexibility for negotiating sharp tortuous regions in vessels, as for example, coronary vessels. The use and operation of the device shown in FIGS. 6 and 7 is identical to that hereinbefore described for the previous embodiment.

It is apparent from the foregoing that there has been provided an imaging balloon dilatation catheter which makes it possible to perform angioplasty procedures in a conventional manner but which in addition makes it possible immediately thereafter to image the results of the procedure to see whether or not it is satisfactory and if not, to permit a further attempt to further enlarge the opening in the stenosis before withdrawing the catheter from the vessel of the patient. The catheter is constructed in such a manner so that it can negotiate rather tortuous vessels and is particularly adapted for use in the cardiovascular system although other vessels in the vascular system of a patient can be treated in the same manner with the catheter.

What is claimed is:

1. An imaging angioplasty catheter having proximal and distal ends, the catheter comprising:
   an elongated flexible tubular member having proximal and distal extremities and having first and second light lumens which are non-coaxial in relation to each other and having a guidewire lumen extending longitudinally therein;
   an inflatable dilation balloon carried by said tubular member such that it is located between the proximal and distal ends of the catheter and is disposed near the distal extremity of the tubular member and which is adapted to dilate an arterial stenosis and which has an interior in fluid communication with at least one of the light lumens;
   illuminating optical fiber means disposed in the first light lumen and extending to the distal end of the catheter through the length of the tubular member;
   an imaging optical fiber means disposed in the second light lumen and extending adjacent the distal end of the catheter through the length of the tubular member; and
   a lens for supplying an image to said imaging optical fiber means;
   wherein the guidewire lumen is adapted to receive a guidewire therein and to direct fluid therethrough.

2. A catheter as in claim 1 wherein an adapter is secured to the proximal extremity of the tubular member, said adapter having a plurality of arms, one of said arms including an inflation/deflation port and wherein at least one of the light lumens in the flexible elongated member is in communication with the interior of the balloon and with the inflation/deflation port.

3. A catheter as in claim 2 wherein the lumens in which the illuminating optical fibers are disposed and the set of imaging optical fibers are disposed provide flow passages extending therethrough which are in communication with the interior of the balloon and which are in communication with the inflation/deflation port.

4. A catheter as in claim 2 together with an additional elongate flexible member extending through one of the arms of the adapter and wherein the illumination optical fibers and the set of imaging optical fibers extend through the additional elongate flexible member.

5. A catheter as in claim 1 together with self-venting means carried by the distal extremity of the flexible elongate tubular member and the distal extremity of the balloon which permits the escape of air from the interior of the balloon but restricts the escape of liquid from the interior of the balloon.

6. A catheter as in claim 1 together with markers identifying certain regions of the balloon.

7. The catheter of claim 1 wherein the interior of the balloon is in fluid communication with both of the light lumens.

8. The catheter of claim 1 further comprising a cutout which places said at least one light lumen in fluid communication with the interior of the balloon, the cutout comprising:

an elongated, cutaway portion of the tubular member along a substantial length thereof disposed within the interior of the balloon which opens said at least one light lumen to the interior of the balloon.

9. The catheter of claim 8 wherein the cutout places both light lumens in fluid communication with the interior of the balloon and comprises:

an elongated, cutaway portion of the tubular member along a substantial length thereof disposed within the interior of the balloon which opens both light lumens to the interior of the balloon.

10. An imaging balloon dilation catheter having proximal and distal ends, the catheter comprising:

an elongated flexible tubular member having first and second longitudinal light lumens which are non-coaxial in relation to each other and having a longitudinal guidewire lumen;

an inflatable balloon carried by said flexible tubular member such that it is located between the proximal and distal ends of the catheter and is disposed near the distal end of the tubular member, the balloon adapted to dilate an arterial stenosis;

an illuminating optical fiber means disposed in the first light lumen and extending to the distal end of the catheter therethrough, said first lumen in communication with the interior of said inflatable balloon;

an imaging fiber optic means disposed in the second light lumen and extending adjacent the distal end of the catheter therethrough;

means to provide an image to the distal end of said imaging optical fiber; and the guidewire lumen is adapted to receive a guidewire therein and to direct fluid therethrough.

11. The imaging balloon dilation catheter of claim 10 wherein said first and said second lumens are adapted to inflate and deflate said balloon.

12. The imaging balloon dilation catheter of claim 10 wherein said means to provide an image to the distal end of said imaging optical fiber member comprises a lens.

13. The imaging balloon dilation catheter of claim 12 wherein said lens is spaced apart from the distal end of said imaging optical fibers.

14. The imaging balloon dilation catheter of claim 12 wherein said lens is mounted on a portion of said tubular member adjacent the distal end of said imaging fibers.

15. The catheter of claim 10 wherein the interior of the balloon is in fluid communication with both of the light lumens.

16. The catheter of claim 10 further comprising a cutout which places said at least one light lumen in fluid communication with the interior of the balloon, the cutout comprising:

an elongated, cutaway portion of the tubular member along a substantial length thereof disposed within the interior of the balloon which opens said at least one light lumen to the interior of the balloon.

17. The catheter of claim 16 wherein the cutout places both light lumens in fluid communication with the interior of the balloon and comprises:

an elongated, cutaway portion of the tubular member along a substantial length thereof disposed within the interior of the balloon which opens both light lumens to the interior of the balloon.

18. An imaging balloon catheter which has proximal and distal ends comprising:

an elongated catheter body having distal and proximal extremities and first and second longitudinal, non-coaxial light lumens and a longitudinal guidewire lumen therein;

a dilatation balloon located between the proximal and distal ends of the catheter and disposed near the distal extremity of said catheter body which is adapted to dilate an arterial stenosis and which has an interior in fluid communication with at least one of said light lumens;

the first light lumen adapted to house an illuminating optical fiber assembly and to inflate and deflate the dilatation balloon located near the distal end of said catheter;

the second light lumen adapted to house an imaging optical fiber assembly; and the guidewire lumen has an internal diameter which is sufficiently large to receive a guidewire and to direct fluid therethrough when a guidewire is disposed within said lumen.

19. The imaging balloon catheter of claim 18 wherein said catheter further comprises venting means in said balloon to allow the escape of air from said balloon when a fluid is pumped into the balloon, but which resists the escape of fluid from said balloon.

20. The imaging balloon catheter of claim 18 wherein said illuminating optical fiber assembly further comprises a plurality of optical fibers.

21. The imaging balloon catheter of claim 18 which further comprises an adapter secured to the proximal end of said tubular member, said adapter including means to connect an inflation/deflation apparatus to a lumen connected to the interior of said balloon.

22. The imaging balloon catheter of claim 21 which further comprises means in said adapter to connect said imaging optical fiber assembly to external viewing means.

23. The imaging balloon catheter of claim 21 which further comprises means in said adapter to connect said illuminating optical fibers to an external source of light.

24. The imaging balloon catheter of claim 21 which further comprises means in said adapter to introduce a flushing liquid into the guidewire lumen.

25. The imaging balloon catheter of claim 18 wherein said imaging optical fiber assembly further comprises an imaging lens attached to the distal end of said imaging optical fiber assembly.

26. The imaging balloon catheter of claim 2 wherein said lens is attached to the distal end of said imaging optical fiber assembly such that a gap exists between the proximal face of said lens and the distal end of said optical fibers.

27. The imaging balloon catheter of claim 25 wherein said imaging lens is attached to the distal end of said imaging optical fiber assembly by a transparent adhesive material.

28. The catheter of claim 18 wherein the interior of the balloon is in fluid communication with both of the light lumens.

29. The catheter of claim 18 further comprising a cutout which places said at least one flight lumen in fluid communication with the interior of the balloon, the cutout comprising:
an elongated, cutaway portion of the tubular member along a substantial length thereof disposed within he interior of the balloon which opens said at least one light lumen to the interior of the balloon.

30. The catheter of claim 29 wherein the cutout places both light lumens in fluid communication with the interior of the balloon and comprises:
an elongated, cutaway portion of the tubular member along a substantial length thereof disposed within the interior of the balloon which opens both light lumens to the interior of the balloon.

31. A method of performing an angioplasty procedure in a patient's vasculature which comprises:
advancing a guidewire within a patient's vasculature until the distal portion of said guidewire crosses a lesion to be reduced;
advancing a dilatation catheter with a dilatation balloon disposed between the proximal and distal ends of the catheter and disposed near the distal end thereof within the patient's vasculature over the guidewire until the distal portion of said catheter is disposed proximally from said lesion by disposing the guidewire in a longitudinal guidewire lumen formed in the catheter;
flushing the area distal of said catheter with a fluid which is essentially transparent to light by passing said fluid through a space between the guidewire and the interior wall of the guidewire lumen within the catheter which houses the guidewire;
illuminating said lesion and imaging said lesion at the distal end of said catheter by means of an imaging system disposed in first and second non-coaxial, longitudinal light lumens in said catheter;
further advancing said catheter over said guidewire to dispose the dilatation balloon disposed on said catheter within said lesion;
forming a passage between at least one light lumen and the interior of the balloon;
inflating said balloon to dilate said lesion by introducing an inflation medium into said at least one light lumen having the passage in fluid communication with the interior of the balloon;
deflating the dilatation balloon;
withdrawing said catheter until the distal end of the catheter is proximal to said lesion; and
again illuminating said lesion and imaging said lesion by means of the imaging system in said catheter.

32. The method of claim 31 wherein the step of forming a passage between at least one light lumen and the interior of the balloon comprises the step of forming a passage between both light lumens and the interior of the balloon.

33. The method of claim 31 wherein the step of forming a passage includes the step of cutting away a portion of the tubular member along a length thereof positioned inside the balloon to open at least one light lumen and place the interior of the balloon in fluid communication with said opened at least one light lumen.

34. The method of claim 31 wherein the step of forming a passage includes the step of cutting away a portion of the tubular member along a length thereof portioned inside the balloon to open both light lumens and place the interior of the balloon in fluid communication with both light lumens.

35. The method of claim 34 wherein the step of cutting away includes cutting away a substantial portion of the tubular member along it length disposed inside the balloon.

36. An imaging angioplasty catheter having proximal and distal ends, the catheter comprising:
an elongated flexible body member having proximal and distal extremities, said distal extremity located proximal from the distal end of the catheter, and having first and second light lumens formed longitudinally therein which are non-coaxial in relation to each other and having a guidewire lumen;
illuminating optical fiber means disposed in the first light lumen through the length of the body member and extending past the distal extremity of the body member to the distal end of the catheter;
an imaging optical fiber disposed in the second light lumen through the length of the body member and extending past the distal extremity of the body member and ending adjacent the end of the catheter;
a lens for supplying an image to said imaging optical fiber means;
an inflatable dilatation balloon disposed at its proximal end at the distal extremity of the body member and at its distal end at a position adjacent the distal end of the catheter and which is adapted to dilate an arterial stenosis and which has an interior in fluid communication with both of the light lumens; and
a guidewire tube connected to the guidewire lumen at the distal extremity of the catheter body and extending to the distal end of the catheter;
wherein the guidewave lumen and guidewave tube are adapted to receive a guidewire therein and to direct fluid therethrough simultaneously.

37. The catheter of claim 36 wherein the lens is disposed at a position proximal to the distal end of the catheter.

* * * * *

UNITED STATES PATENT AND TRADEMARK OFFICE
CERTIFICATE OF CORRECTION

PATENT NO. : 5,090,959
DATED : February 25, 1992
INVENTOR(S) : Samson, Aita It is certified that error appears in the above-identified patent and that said Letters Patent is hereby corrected as shown below:

Column 10, line 16 (claim 34), change "portioned" to --positioned--.

Column 10, line 53 (claim 36), change "guidewave" to --guidewire-- (each occurrence).

Signed and Sealed this

Fifteenth Day of June, 1993

Attest:

MICHAEL K. KIRK

Attesting Officer

Acting Commissioner of Patents and Trademarks